United States Patent
Tenerz et al.

(10) Patent No.: US 7,472,601 B1
(45) Date of Patent: Jan. 6, 2009

(54) SENSOR FOR INTRAVASCULAR MEASUREMENTS WITHIN A LIVING BODY

(75) Inventors: Lars Tenerz, Uppsala (SE); Leif Smith, Uppsala (SE)

(73) Assignee: Radi Medical Systems AB, Uppsala (SE)

( * ) Notice: Subject to any disclaimer, the term of this patent is extended or adjusted under 35 U.S.C. 154(b) by 0 days.

(21) Appl. No.: 11/902,508

(22) Filed: Sep. 21, 2007

(51) Int. Cl.
    *A61B 5/00* (2006.01)
(52) U.S. Cl. .......................................... 73/756; 600/585
(58) Field of Classification Search .................. 73/700, 73/756
    See application file for complete search history.

(56) References Cited

U.S. PATENT DOCUMENTS

| | | |
|---|---|---|
| RE35,648 E | 11/1997 | Tenerz et al. |
| 6,343,514 B1 | 2/2002 | Smith |
| 2004/0225232 A1 * | 11/2004 | Malmborg et al. .......... 600/585 |
| 2005/0000294 A1 * | 1/2005 | Tenerz et al. ................. 73/727 |
| 2005/0011272 A1 * | 1/2005 | Tenerz .......................... 73/756 |
| 2005/0268724 A1 * | 12/2005 | Tenerz .......................... 73/753 |
| 2005/0268725 A1 * | 12/2005 | Tulkki .......................... 73/756 |
| 2006/0207335 A1 * | 9/2006 | Tenerz et al. ................. 73/754 |
| 2007/0106142 A1 * | 5/2007 | Von Malmborg et al. .... 600/373 |
| 2007/0106165 A1 * | 5/2007 | Tulkki ......................... 600/486 |
| 2007/0255145 A1 * | 11/2007 | Smith et al. ................. 600/485 |
| 2008/0132806 A1 * | 6/2008 | Smith .......................... 600/585 |

OTHER PUBLICATIONS

R. He et al., "Giant piezoresistance effect in silicon nanowires," Letters, vol. 1, Oct. 2006, pp. 42-46.

* cited by examiner

*Primary Examiner*—Andre J Allen
(74) *Attorney, Agent, or Firm*—Foley & Lardner LLP

(57) ABSTRACT

The invention relates to a sensor and guide wire assembly for intravascular measurements within a living body, wherein a sensor element, which is arranged at a distal portion of a guide wire, comprises at least one piezoresistive nanowire.

8 Claims, 4 Drawing Sheets

SENSOR FOR INTRAVASCULAR MEASUREMENTS WITHIN A LIVING BODY

FIELD OF THE INVENTION

The invention relates generally to a pressure sensor mounted on a guide wire for intravascular measurements of pressure in a living body, and in particular to the design of a piezoresistive element, which is part of the pressure sensor and whose piezoresistive effect is utilized for pressure measurements.

BACKGROUND OF THE INVENTION

Sensor and guide wire assemblies in which a sensor, adapted for measurements of physiological variables in a living body, such as blood pressure and temperature, is mounted at a distal portion of a guide wire are known.

For example, the U.S. Pat. No. Re. 35,648, which is assigned to the present assignee and incorporated herein by reference for the devices and techniques disclosed therein, discloses a sensor and guide wire assembly comprising a sensor element, an electronic unit, signal transmitting cables connecting the sensor element to the electronic unit, a flexible tube having the signal cables and the sensor element disposed therein, a solid metal wire, and a coil attached to the distal end of the solid wire. The sensor element comprises a pressure sensitive device, e.g. a membrane, with a piezoresistive element electrically connected in a Wheatstone bridge-type of circuit arrangement mounted thereon. Examples of Wheatstone bridge-arrangements can be found in the U.S. Pat. No. 6,343,514, which is assigned to the present assignee and the contents of which are incorporated herein by reference for devices and techniques disclosed therein.

In a sensor and guide wire assembly comprising this type of piezoresistive element, the piezoresistive element is typically made from a doped silicon sheet and exhibits sensitivity on the order of 20 m$\Omega$/mmHg, i.e. the resistance of the piezoresistive element changes by 20 m$\Omega$ when the ambient pressure changes by 1 mmHg. To be able to reliably detect such a small change in resistance, it is consequently required that all other resistances, both the ones that are mounted in the Wheatstone bridge and the ones that accidentally can appear between different components and between components and surrounding matter (e.g. blood), are controlled within less than 20 m$\Omega$. In other words, the rather low sensitivity may potentially affect the reliability of the pressure measurements made by this type of blood pressure sensor, and therefore imparts very high requirements on the production processes of the corresponding sensor and guide wire assembly, something which adds to the production costs. The rather low sensitivity of the conventional sensor element also requires that the dimensions of the membrane, on which the sensor element is mounted, are relatively large, because a large membrane will deflect more than a small membrane, and a large membrane will therefore subject a sensor element mounted thereon to more stress. For various reasons there is, however, an ever ongoing struggle to reduce the dimensions of a sensor guide wire, and the conventional sensor elements therefore present a hindrance in these efforts.

Consequently, there is still a need for an improved guide wire mounted pressure sensor, by which pressure measurements can be performed with higher sensitivity. Another need is to provide a sensor element with higher sensitivity such that a sensor and guide wire assembly with smaller dimensions can be produced.

SUMMARY OF THE INVENTION

In one embodiment of the present invention, a Wheatstone bridge-type of arrangement is disclosed, wherein, however, a conventional piezoresistive element has been replaced by a so-called nanowire. A nanowire is a wire having dimensions of the order of one nanometer ($10^{-9}$ meters), and can be defined as a structure that has a lateral size constrained to tens of manometers or less and an unconstrained longitudinal size. A nanowire can be made from carbon (C) or a metal, such as nickel (Ni), platinum (Pt), or gold (Au); or a semiconductor, such as silicon (Si), indium phosphide (InP), or gallium nitride (GaN); or insulators like silicon dioxide ($SiO_2$) and titanium dioxide ($TiO_2$). Several of these nanowires exhibit a pronounced piezoresistive behaviour, which in the field also is referred to as the giant piezoresistance effect. The piezoresistive behaviour is usually due to a change in conductance when the nanowire is subjected to stress caused by stretching and/or compression. According to the invention, a guide wire mounted sensor comprises a sensor element, which, in turn, comprises at least one nanowire exhibiting a piezoresistive effect, which is exploited in order to improve the sensitivity of the sensor. As defined herein, it should further be noted that the term "piezoresistive nanowire" also encompasses nanowires made from materials that do not exhibit a piezoresistance effect in themselves; examples of such materials are zinc oxide (ZnO) and aluminium nitride (AlN). In nanowires made from these materials, the piezoresistive behaviour is believed to be caused by a charge rearrangement, which takes place when the nanowire is subjected to stress. Generally, the term "piezoresistive nanowire" as used herein encompasses all kinds of nanowires and wire-like structures such as nanowhiskers, nanorods, nanotubes, nanocantilevers, etc. whose electrical resistance changes when they are deformed (e.g. compressed or stretched) due to the influence of pressure. It should also be noted that a nanowire according to the invention can have any cross-sectional shape. In a preferred embodiment, the cross-section is solid and circular, but it is also contemplated that a nanowire can have a ring-shaped cross-section, i.e. the nanowire is in fact a nanotube. In another embodiment, the cross-section could be quadratic or rectangular. In the latter case, the nanowire could have the shape of a thin and flat strip. The latter embodiment could be advantageous not least from a production point of view.

According to different embodiments of the invention, one or several nanowires can be arranged in different constellations. In one embodiment, a nanowire is disposed on a membrane, similar to the arrangement disclosed in the above-referenced U.S. Pat. No. 6,343,514, such that the nanowire is stretched when the membrane deflects due to the influence of an ambient pressure (typically the blood pressure). In another embodiment, a nanowire is positioned beneath a membrane, such that a first end of the nanowire is connected to the underside of the membrane while the second end of the nanowire is supported by the bottom surface of a recess, which is covered by the membrane. By this arrangement, the nanowire is compressed when the membrane deflects due to influence from external pressure. In a further embodiment, a double-layered membrane is provided, wherein one or several nanowires are provided in the space between the two layers. In a further embodiment, at least one nanowire is arranged along the underside of membrane, such that the nanowire is deformed when the membrane deflects due to influence of an ambient pressure.

A nanowire is characterized by having a piezoresistivity which depends on parameters like diameter, length and degree of doping as well as orientation. For typical parameters, a nanowire can have a resistivity on the order of 0.1 MΩ to 10 MΩ. As will be more clearly explained below, due to the rather low sensitivity of the sensor, such a high resistivity puts corresponding requirements on the insulation of the sensor element and also on other parts of the sensor and guide wire assembly. The insulation of other conducting elements in the sensor and guide wire assembly should be approximately four orders of magnitude larger than the resistivity of the nanowire, i.e. on the order of 1 GΩ to 100 GΩ. By arranging several nanowires in a parallel relationship, the total resistance of the nanowire arrangement is reduced, leading to a corresponding reduction of the insulation required for other elements in the sensor and guide wire assembly. In embodiments of the present invention, the number of nanowires being arranged in a parallel relationship may be varied, and is determined by the total resistivity of the nanowire arrangement in relation to the desired sensitivity as well as insulation characteristics of the rest of the sensor and guide wire assembly.

DETAILED DESCRIPTION OF PREFERRED EMBODIMENTS

Figure 1:
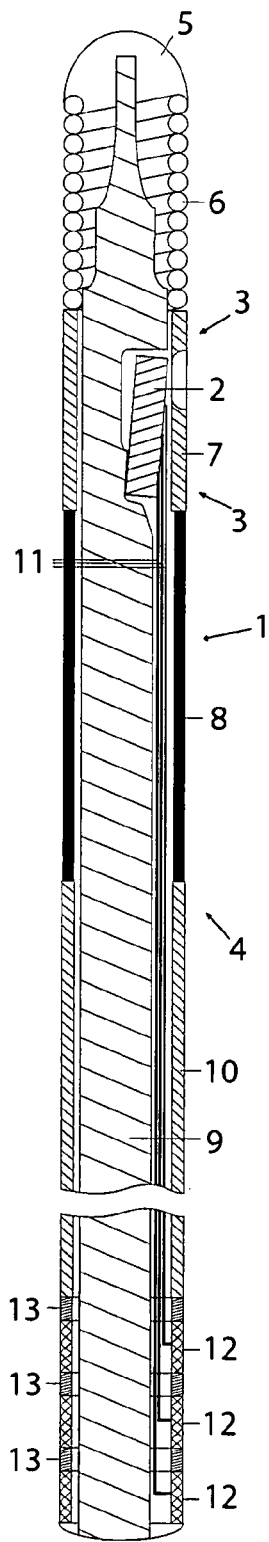
FIG. 1 is a schematic illustration of a sensor and guide wire assembly according to the prior art.

FIG. 1 illustrates schematically the general design of a sensor and guide wire assembly 1 according to the prior art. The sensor and guide wire assembly 1 comprises a sensor element 2, which is arranged in a distal portion 3 of a sensor guide wire 4. More specifically, the sensor guide wire 4 comprises a distal tip 5, a distal coil spring 6, a jacket or sleeve 7, a flexible distal tube 8, which alternatively could be in the form of a coil spring, a core wire 9, and a proximal tube 10. The distal coil spring 6 is attached to the distal tip 5, and extends to the jacket 7, which serves as a housing for the sensor element 2. The flexible distal tube 8 extends between the jacket 7 and the proximal tube 10. The sensor element 2 is mounted in a recess in a distal portion of the core wire 9, and is through a window in the jacket 7 in fluid communication with the medium, e.g. blood, surrounding the sensor and guide wire assembly 1. The sensor and guide wire assembly 1 comprises further a number of signal transmitting cables 11, the distal ends of which are electrically connected to the sensor element 2 and which extend along the core wire 9 to the proximal end portion of the sensor guide wire 4, where each signal transmitting cable 11 is electrically connected to a conductive member 12. The conductive members 12 are electrically insulated from the core wire 9 as well as from each other by insulating members 13, so as to form a male connector adapted for connection to a corresponding female connector of an external signal conditioning and display unit (not shown in FIG. 1) for displaying the measured quantities, e.g. pressure, temperature and/or flow.

Figure 2:
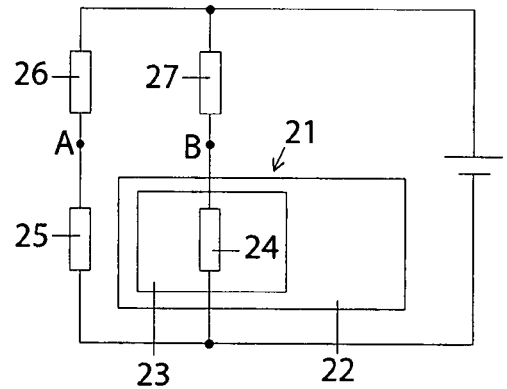
FIG. 2 is a schematic illustration of a first Wheatstone-bridge arrangement according to the prior art.

An exemplary sensor element 21 is illustrated in FIG. 2. Here the sensor element 21 comprises a sensor support body in the form of a silicon chip 22, in which there is a cavity made (not visible in FIG. 2), e.g. by etching. Across the cavity there is formed a thin polysilicon membrane 23 having a thickness of e.g. 0.4-1.5 μm and a side length of about 100 μm. In contact with the membrane 23 there is mounted a piezoresistive element 24. External pressure (typically blood pressure) acting on the membrane 23 will cause deflection of the membrane 23, which in turn will change the resistivity of the piezoresistive element 24. Since the piezoresistive element 24 is part of a Wheatstone bridge, which also comprises resistors 25, 26 and 27, the voltage between terminals A and B will change and the corresponding electrical output signal can be detected. It should be mentioned that resistors 25, 26 and 27 in this version are disposed externally of the sensor element 21, and do not form part of the sensor element 21. By individual calibration parameters stored in a female connector, which is part of a sensor and guide wire assembly comprising the sensor element 21, and a calibration procedure initiated at the start of the measurement, the output signal is converted to a pressure value in an external unit, and the present pressure is displayed on a screen.

From FIG. 2 it can be appreciated that the insulation requirements on the sensor element 21 are high. If, for example, electrical current could flow around the piezoresistive element 24, instead of through the piezoresistive element 24, the change in resistance, which a pressure change would cause, would not be detectable. A low sensitivity of the piezoresistive element makes it even more necessary to prevent the electrical current from flowing outside of the piezoresistive element 24. In other words, the higher resistance of a sensor element, the higher is the insulation requirement for the other parts of the sensor element; and the lower sensitivity of a sensor element, the higher is the insulation requirement.

Figure 3:
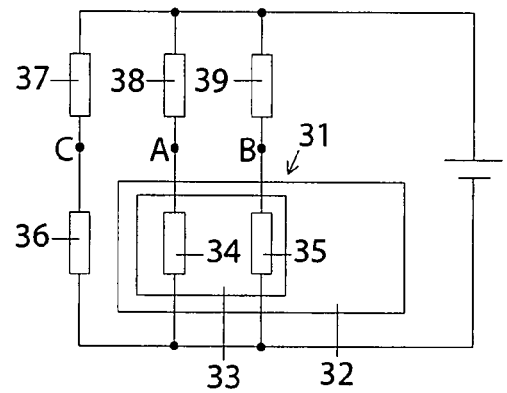
FIG. 3 is a schematic illustration of a second Wheatstone-bridge arrangement according to the prior art.

As is well-known, resistors are usually temperature sensitive, and to provide for compensation of effects induced by temperature changes, a double Wheatstone-bridge has been suggested, and is illustrated in FIG. 3. Here, a sensor element 31 comprises a silicon chip 32, in which a cavity (not visible in FIG. 3) has been made. Over the cavity a membrane 33 is arranged, and on the membrane 33 two resistors 34 and 35 are mounted. The resistor 34, which also is referred to as the active resistor 34, is temperature as well as pressure sensitive, whereas the resistor 35, which is also referred to as the reference resistor 35, is only temperature sensitive. The double Wheatstone bridge comprises further resistors 36, 37, 38 and 39, which in this embodiment are disposed externally of the sensor element 31, and do not form part of the sensor element 31. By comparison of the output voltages between terminals A-B and B-C, respectively, the temperature induced effects on the resistivities can be compensated for.

It should be stressed that the two bridge circuits illustrated above only are exemplifying. In practice there are numerous different ways of arranging a piezoresistive element such that its intrinsic pressure dependent resistivity can be employed for pressure measurements; and although different types of bridge circuits possess many advantageous features, it is by no means mandatory to utilize a bridge circuit, as the person skilled in the art will appreciate.

Figure 4A:
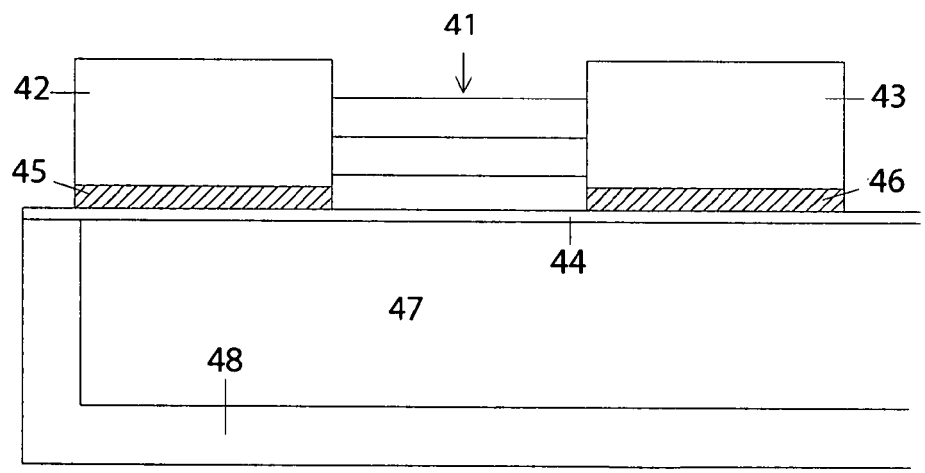
FIGS. 4a-c illustrate schematically a first embodiment of a sensor element comprising at least one nanowire according to the present invention.

The present invention is directed to a sensor and guide wire assembly comprising a piezoresistive element in the form of a nanowire. In a first embodiment of the invention, at least one nanowire is arranged on a membrane in a way similar to the arrangements shown in conjunction with FIG. 2 and FIG. 3, respectively. More specifically, FIG. 4a (which is a side view) and b (which is a top view) illustrate schematically how several piezoresistive nanowires 41 (in this case nine nanowires) extend between a first terminal 42 and a second terminal 43, which are attached to the upper side of a flexible membrane 44, from which the terminals 42 and 43 are electrically insulated by insulating layers 45 and 46, respectively. The membrane 44 covers an evacuated cavity 47 made in a chip 48 made from, for example, silicon; and when the membrane 44 deflects due to influence from the ambient pressure (e.g. blood pressure), the nanowires 41 will be stretched, and their (total) electrical resistance will thereby change. This resistance change is detected by a suitable electrical circuit, of which the terminals 42, 43 as well as the nanowires 41 are parts. An output signal is, for example, generated in a way very similar to the bridge arrangements shown in FIGS. 2 and 3, respectively, but also other ways of generating an output signal which is dependent on the applied pressure are possible. The number of piezoresistive nanowires 41 is optional, and can vary from one to several thousands. As the resistance of a nanowire is rather high, a relatively large number of nanowires, which are connected in parallel, may be needed to get a total resistance that is acceptable, as was discussed above. It can be noted that in FIGS. 4a and b, both terminals 42 and 43 are disposed on top of the membrane 44. It is, however, possible that only one of the terminals 42, 43 is mounted on the membrane 44, while the other is mounted outside of the membrane 44. The position(s) of the terminal (s) that is (are) mounted on a membrane is optional, but generally the relative deflection is largest near the edges of the membrane, and it can therefore be advantageous to mount the terminal(s) near the border of the membrane. In particular, it may be advantageous to mount one terminal outside the membrane and mount the other terminal close to the edge of the membrane. In a preferred embodiment, a nanowire arrangement is electrically insulated from the ambient fluid (typically blood); and in FIG. 4c the nanowires 41 as well as the terminals 42, 43 are covered by a thin film 49. The film 49, which is very schematically indicated in FIG. 4c, could be made from e.g. silicon or an insulating material. It is also possible to cover a nanowire and terminal arrangement with a thin layer of, for example, silicon oxide (SiO) or aluminium nitride (AlN), or another insulator.

Figure 4B:
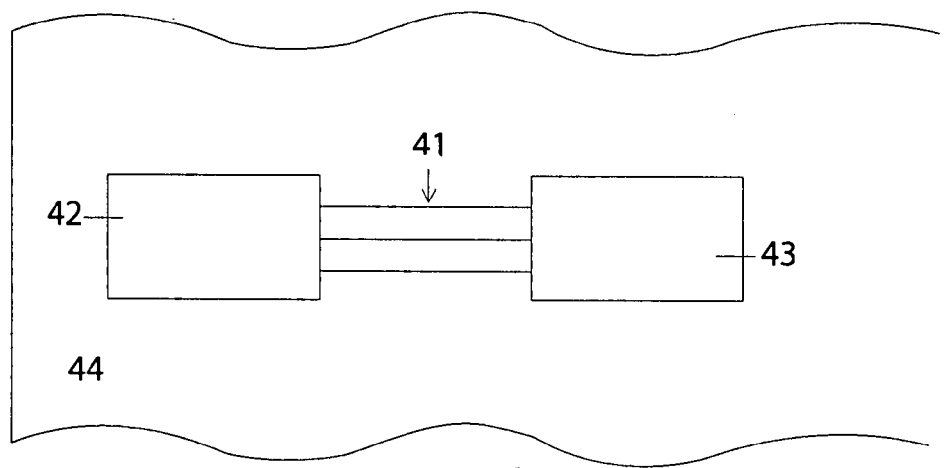

As already stated, the number of nanowires is optional and the nanowires can be arranged in any kind of constellation. From FIGS. 4a and 4b it may be inferred that several nanowires could be arranged side-by-side close to each other in two dimensions, such that a beam-shaped structure comprising a large number of nanowires is provided. Such a beam-shaped structure could have any cross-sectional shape, including rectangular and circular. A beam made from a large number of nanowires could be relatively easy to handle during the assembly of a sensor and guide wire assembly. Each of the nanowires is preferably insulated from the other nanowires.

Figure 5A:
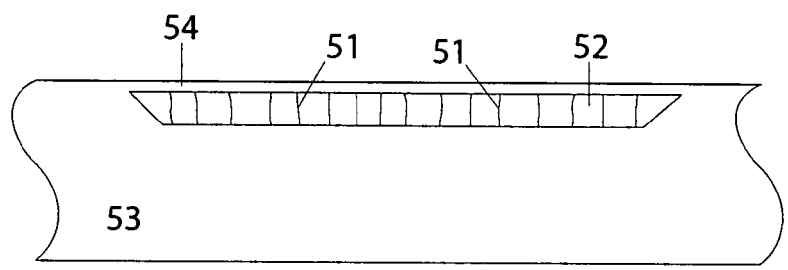
FIGS. 5a-b illustrate schematically a second embodiment of a sensor element comprising at least one nanowire according to the present invention.
Figure 5B:
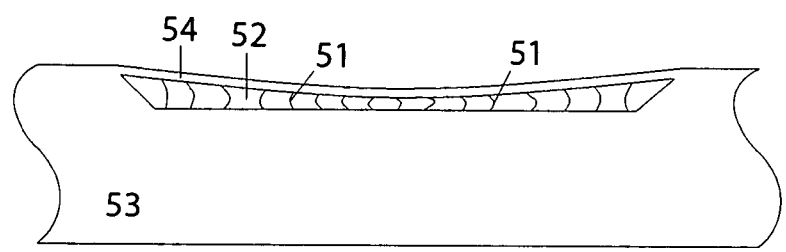

In FIGS. 5a and 5b a second embodiment of the present invention is disclosed. Here, a number of piezoresistive nanowires 51 (in this case sixteen nanowires) have been arranged within a cavity 52 created by a recess in a chip 53, which recess is covered by a membrane 54. More specifically, the nanowires 51 extend between the bottom surface of the cavity 52 and the membrane 54, such that when the membrane 54 deflects downwards due to influence of the ambient pressure (typically blood pressure), the nanowires 51 are compressed (see FIG. 5b), which leads to a corresponding change in their total resistance. The resistance change can be exploited to determine the applied pressure.

Figure 6:
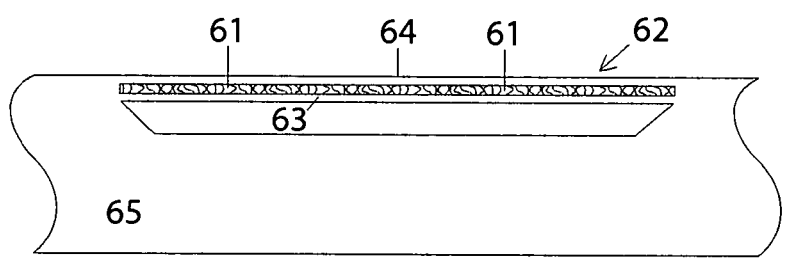
FIG. 6 illustrates schematically a third embodiment of a sensor element comprising at least one nanowire according to the present invention.

FIG. 6 shows a third embodiment of the present invention, wherein a large number of piezoresistive nanowires 61 are arranged within a double-walled membrane 62, which comprises an inner wall 63 and an outer wall 64. The membrane 62 covers a recess which has been made in a chip 65. Like before, deflection of the membrane 62 will cause the nanowires 61 to compress, which, in turn, leads to a resistance change that can be detected by a suitable electrical circuit.

Figure 4C:
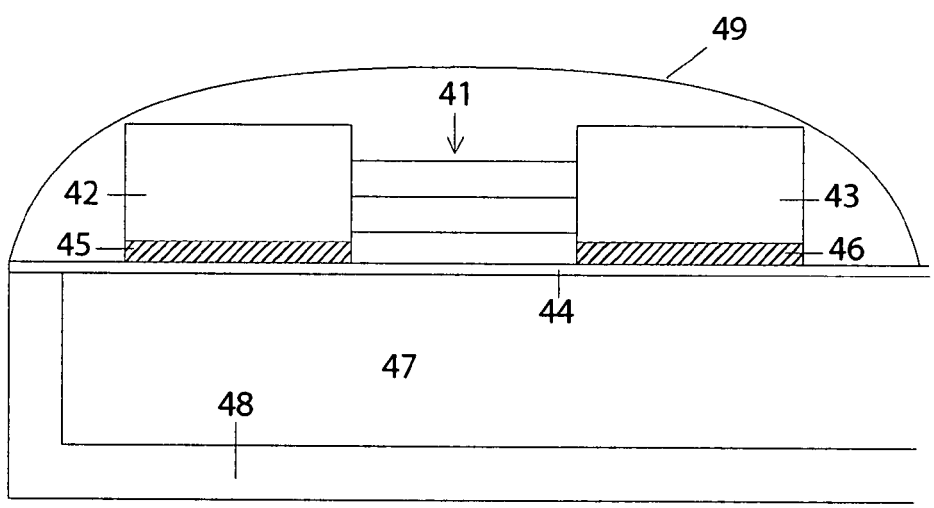

As was explicitly discussed in conjunction with FIG. 4c, it can be advantageous to provide the nanowires with some insulation against ambient fluid. The insulation problem can be solved by arranging the nanowires beneath a flexible membrane; and in FIG. 7 an exemplifying embodiment of such an arrangement is disclosed. In this embodiment, several nanowires 71 extend between a first terminal 72 and a second terminal 73, which are attached to the underside of a flexible membrane 74, from which the terminals 72 and 73 are electrically insulated by insulating layers 75 and 76, respectively. The membrane 74 covers an evacuated cavity 77 made in a chip 78; and when the membrane 74 deflects due to influence from the ambient pressure (e.g. blood pressure), the nanowires 71 will be compressed, and their (total) electrical resistance will thereby change. This resistance change can be detected by an electrical circuit, of which the terminals 72, 73 as well as the nanowires 71 are parts. An output signal can, for example, be generated in a way very similar to the bridge arrangements shown in FIGS. 2 and 3, respectively, but also other ways of generating an output signal which is dependent on the applied pressure are possible. Also in this embodiment, the chip 78 can be made from silicon; it may, however, be advantageous to make the chip 78 from an insulator such as glass, because electrical conductive paths, which electrically contact the terminals 72, 73, can then be provided in the surface of the glass chip 78.

Figure 7:
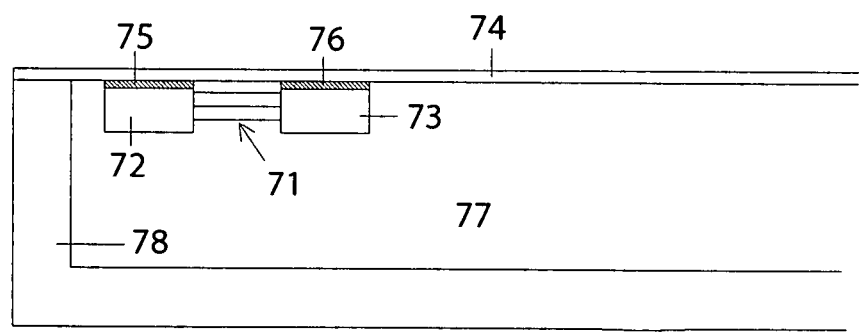
FIG. 7 illustrates schematically a fourth embodiment of a sensor element comprising at least one nanowire according to the present invention.

Also when a nanowire arrangement is disposed at the underside of a membrane, rather than on the upper side of a membrane, the positions of the nanowires and corresponding terminals are optional, but it can be advantageous to mount the nanowires close to an edge of the membrane, because the relative stress is largest close to the border of a membrane. In this context it may, however, be noted that when a nanowire arrangement, like the nanowire arrangement illustrated in FIG. 7, is disposed near the edge of a membrane, the nanowires are compressed when the membrane deflects downwards due to the influence of the ambient pressure. When, on the other hand, a nanowire arrangement, like the nanowire arrangement illustrated in FIG. 7, instead is disposed close to the centre of a membrane, the nanowires are stretched when the membrane deflects downwards due to the influence of the ambient pressure. If nanowires are used which exhibit one piezoresistive effect when they are compressed and another piezoresistive effect when they are stretched, the position of the nanowires on a membrane should preferably be chosen such that the largest piezoresistive effect is obtained.

Figure 8:
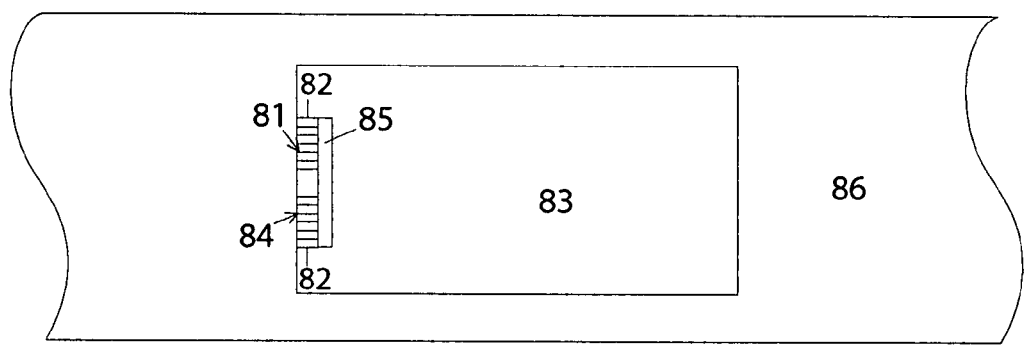
FIG. 8 illustrates schematically a fifth embodiment of a sensor element comprising at least one nanowire according to the present invention.

In FIG. 8 another embodiment of the present invention is shown, wherein a first set 81 of nanowires 82 is arranged at an edge of the upper side of a membrane 83, and wherein a second set 84 of piezoresistive nanowires 82 is arranged at the same edge of the membrane 83 but with a distance from the first set 81 of nanowires 82. The first set 81 of nanowires 82 and the second set 84 of nanowires 82 are electrically connected by a connector 85. The membrane 83 covers a cavity made in, for example, a silicon chip 86, such that when the membrane 83 deflects downwards, the piezoresistive nanowires 82 are stretched, which, in turn, changes the (total) resistance of the nanowire arrangement. In this embodiment, the length of the nanowires could be of about 10 nm to 200 nm, while the length of the connector is about 1 μm to 10 μm. A similar arrangement can as an alternative be provided at the underside of a membrane, which covers, for example, a glass chip.

Nanowires for use in the different embodiments of a sensor element for sensor and guide wire assemblies can be produced by different methods, which are well known in the art. One method of producing nanowires is to let the nanowires, e.g. silicon nanowires, grow on the surface of a silicon-on-insulator (SOI) substrate having a suitable orientation. Another way of producing nanowires is to etch out thin strips from, for example, a silicon wafer. In the latter case, these thin strips then form bridges lying side-by-side in a multilayer arrangement.

Although the present invention has been described with reference to specific embodiments, it will be apparent for those skilled in the art that many variations and modifications can be done within the scope of the invention as described in the specification and defined with reference to the claims below.

What is claimed is:

1. A sensor for intravascular measurement within a living body, comprising:
    a guide wire,
    a sensor element, which is arranged at a distal portion of the guide wire, wherein the sensor element comprises at least one piezoresistive nanowire.

2. A sensor according to claim 1, wherein the sensor element comprises a flexible membrane and said at least one piezoresistive nanowire is connected to the flexible membrane such that deflection of the membrane will cause compression or stretching of said at least one piezoresistive nanowire.

3. A sensor according to claim 1, wherein several piezoresistive nanowires are connected in parallel.

4. A sensor according to claim 1, wherein at least one nanowire extends between two terminals, of which at least one is attached to the upper side of a flexible membrane.

5. A sensor according to claim 1, wherein at least one nanowire extends between a bottom surface of a cavity made in a chip and a membrane, which covers said cavity.

6. A sensor according to claim 1, wherein at least one nanowire extends between a first wall and a second wall, which first and second walls constitute the walls of a double-walled membrane, which covers a cavity made in a chip.

7. A sensor according to claim 1, wherein at least one nanowire extends between two terminals, which are attached to the underside of a flexible membrane.

8. A sensor according to claim 1, wherein at least two nanowires extend along a surface portion of a flexible membrane, and said two nanowires are electrically connected by a connector.

* * * * *